United States Patent [19]

Harrison et al.

[11] 4,166,123
[45] Aug. 28, 1979

[54] ACYLAMINOPYRAZOLES

[75] Inventors: Roger G. Harrison, Farnborough; William B. Jamieson, Woking; William J. Ross, Lightwater; John C. Saunders, Maidenhead, all of England

[73] Assignee: Lilly Industries Limited, London, England

[21] Appl. No.: 691,742

[22] Filed: Jun. 1, 1976

[30] Foreign Application Priority Data

Jun. 5, 1975 [GB] United Kingdom ............... 24221/75

[51] Int. Cl.$^2$ .................. A61K 31/415; C07D 231/50
[52] U.S. Cl. ............................... 424/273 P; 548/376; 548/377; 548/374; 542/414; 542/421
[58] Field of Search ............... 260/310 R; 424/273 P; 542/421, 414; 548/376, 377

[56] References Cited

U.S. PATENT DOCUMENTS

| | | | |
|---|---|---|---|
| 2,467,895 | 4/1949 | Kushner et al. | 544/390 |
| 3,457,350 | 7/1969 | Mallen et al. | 424/250 |

FOREIGN PATENT DOCUMENTS 2459380  6/1975  Fed. Rep. of Germany.

OTHER PUBLICATIONS

Eichenberger et al., Helv. Chim. Acta., 48, 1965, p. 524.
The Merk Index, 8th ed., P. G. Stecher Ed., Merk & Co., Inc., Rahway, N.J., 1968, p. 999.

Primary Examiner—Alan L. Rotman
Assistant Examiner—Jane T. Fan
Attorney, Agent, or Firm—Nancy J. Harrison; Everet F. Smith

[57] ABSTRACT

Acylamino pyrazolyl compounds of the formula:

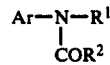

wherein Ar represents an optionally substituted pyrazolyl group, the acylamino group —NR$^1$COR$^2$ being attached to a carbon atom of the pyrazolyl ring, which have anti-allergic activity, methods of making the compounds and pharmaceutical formulations containing the compounds.

26 Claims, No Drawings

ACYLAMINOPYRAZOLES

This invention relates to heterocyclic chemical compounds and more particularly to certain novel 5-membered heteroaryl derivatives having nitrogen atoms as the sole heteroatoms in the ring, substituted by an acylamino group which are useful for the chemotherapy of immediate hypersensitivity conditions and/or which are useful as intermediates in preparing the active derivatives. The invention also includes processes for preparing the active compounds of the invention. Furthermore, the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

A number of acylamino derivatives of five membered heteroaryl systems similar to the compounds of the invention have been previously described —see for example Helv. Chim. Acta., 48, 524 (1965). However, it is to be noted that such prior disclosures of this type of compound have either disclosed a utility quite different from that possessed by the compounds of the invention or have been publications of academic interest only in which no utility whatsoever has been disclosed.

According to the present invention there is provided a novel heteroaryl derivative of the formula:

wherein Ar represents an optionally substituted pyrazolyl group, the acylamino group —$NR^1COR^2$ being attached to a carbon atom of the pyrazolyl ring, $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally substituted phenyl-$C_{1-6}$ alkyl or optionally substituted phenyl-$C_{2-6}$ alkenyl; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally substituted phenyl, optionally substituted phenyl-$C_{1-6}$ alkyl, optionally substituted phenyl-$C_{2-6}$ alkenyl, $C_{1-4}$ alkoxycarbonyl-$C_{1-8}$ alkyl, $C_{2-8}$ carboxyalkyl or $C_{3-6}$ acyloxyalkyl; or $R^1$ and $R^2$ together form a lactam ring having 5 to 7 ring atoms; provided that:
when Ar is a 5-pyrazolyl group, the 1-position of the prazolyl group cannot be substituted by a phenyl group when $R^1$ and $R^2$ are both methyl.

The pyrazolyl nucleus is preferably substituted by one or two groups selected from $C_{1-4}$ alkyl, benzyl, phenyl and halogen.

Preferred $R^1$ substituents are $C_{1-10}$ alkyl, $C_{3-6}$ alkenyl, $C_{3-8}$ cycloalkyl, and benzyl optionally substituted by halogen. Preferred $R^2$ substituents are $C_{1-8}$ alkyl, $C_{2-6}$ alkenyl, $C_{3-10}$ cycloalkyl, phenyl, benzyl, $C_{1-4}$ alkoxycarbonyl-$C_{4-8}$ alkyl, $C_{2-8}$ carboxyalkyl and $C_{3-6}$ acyloxyalkyl.

The term "$C_{1-6}$ alkyl" as used herein means a straight or branched chain alkyl group containing from 1 to 6 carbon atoms such as methyl, ethyl, isopropyl, n-butyl, s-butyl, isobutyl, t-butyl, n-amyl, s-amyl, n-hexyl, 2-ethylbutyl or 4-methylamyl.

Similarly the term "$C_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "$C_{1-4}$ hydroxyalkyl" and "$C_{3-6}$ acyloxyalkyl" mean the aforementioned $C_{1-4}$ alkyl groups substituted with an hydroxy group and acyloxy group respectively. "$C_{2-6}$ alkoxyalkyl" and "$C_{1-6}$ haloalkyl" mean the aforementioned $C_{1-6}$ alkyl groups substituted with an alkoxy group or one or more halogen atoms, such as methoxyethyl, ethoxyethyl, ethoxybutyl, dibromomethyl, trifluoromethyl, 1-chloroethyl, 1,1-dichloroethyl, 1-iodobutyl or pentafluoroethyl.

The term "$C_{3-6}$ alkynyl" is used herein to indicate an alicyclic hydrocarbon group having 3 to 6 carbon atoms which contains a —C≡C— group. However, it should be noted that the —C≡C— group cannot be directly adjacent the nitrogen atom of the acylamino group. Similarly, $C_{3-6}$ alkenyl groups may not contain a —C≡C— group directly adjacent the nitrogen atom.

"$C_{3-10}$ cycloalkyl" means a saturated ring having from 3 to 10 carbon atoms in the ring such as cyclopropyl, cyclobutyl, cyclopentyl, cyclooctyl, or adamantyl. "$C_{3-10}$ cycloalkyl-$C_{1-6}$ alkyl" means the aforementioned saturated rings attached to a $C_{1-6}$ alkylene bridge.

The term "optionally substituted phenyl" as used herein means a phenyl group unsubstituted or substituted by one or more groups which do not substantially alter the pharmacological activity of the compounds of formula (I), such as halogen, trifluoromethyl, methyl, methoxy, or nitro groups.

The term "$C_{2-6}$ carboxyalkyl" as used herein means a $C_{1-5}$ alkyl group substituted by a carboxylic acid group. Examples of such groups are carboxymethyl, carboxyethyl, carboxypropyl and carboxybutyl.

Preferred compounds of the invention are pyrazoles having the structural formula:

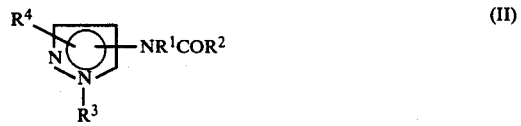

where $R^3$ is a substituent selected from hydrogen, $C_{1-4}$ alkyl and optionally substituted phenyl and $R^4$ is a substituent attached at one of the carbon atoms of the pyrazole nucleus and being selected from formyl, carboxyl, hydroxy, $C_{1-4}$ hydroxyalkyl, $C_{1-4}$ alkyl, $C_{3-10}$ cycloalkyl, $C_{3-6}$ acyloxyalkyl, optionally substituted phenyl and halogen, or is hydrogen.

In another embodiment, compounds of the invention are formula (II) compounds wherein $R^3$ is selected from $C_{1-4}$ alkyl and phenyl and $R^4$ is selected from hydrogen, $C_{1-4}$ alkyl, phenyl and halogen.

Preferably the acylamino group is attached at the 3- or 5-position of the pyrazole nucleus.

Particularly interesting pyrazoles of formula (II) are those wherein $R^3$ is $C_{1-4}$ alkyl, for instance methyl; $R^4$ is hydrogen; $C_{1-4}$ alkyl or phenyl; and $NR^1COR^2$ is a 5-substituent in which $R^1$ is $C_{3-6}$ alkyl, for instance n-butyl and n-hexyl; allyl or benzyl and $R^2$ is $C_{3-6}$ alkyl; for instance i-propyl and n-hexyl; allyl; benzyl or $C_{3-5}$ cycloalkyl. Compounds of formula (I) may be prepared by:

(a) acylating an alkyl derivative of formula:

ArNHR¹     (V)

where Ar and $R^1$ are as defined previously or;

(b) alkylating an acyl derivative of formula:

ArNHCOR² (VI)

where Ar and R² are as defined previously.

The acylation of the compound of formula (V) may be carried out with an acid halide having the formula R²CO—X wherein X is chlorine or bromine and R² is defined above in the presence of a proton acceptor, such as pyridine or triethylamine, in an inert solvent, such as benzene.

The acylation may also be carried out by heating the alkyl derivative of formula (V) with a suitable acid anhydride, (R²CO)₂O, in an inert solvent.

When alkyl derivatives of formula (V) are acylated in which Ar is a heteroaryl nucleus wherein the ring nitrogen atoms are unsubstituted or substituted only by hydrogen, there is a possibility of acylation of a ring nitrogen atoms as well as the exocyclic amino group NHR¹. In such cases, if desired, the acyl group may be removed from the ring by hydrolysis which occurs preferentially at the ring nitrogen atom.

Those skilled in the art will immediately appreciate that a wide variety of other acylating conditions can be used (see, for example, "The Chemistry of Amides" 1971 by A. J. Beckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser, etc.).

Compounds of formula (VI) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula R¹X¹ where X¹ is a reactive atom such as a halogen atom or a reactive group such as an alkyl sulphate group.

Of course, alkylating agents and alkylating reaction conditions other than those specified above can be utilised, the nature of these being readily apparent to those acquainted with the art.

The derivatives of formulae (V) and (VI) can be derived from the corresponding amines of formula ArNH₂ by standard alkylation or acylation techniques.

The amines of formula ArNH₂ are either known compounds, see, for example, *Ang. Chem. Int.* 13. 206 (1974), or can be prepared by modification of known synthetic methods. In the case of pyrazole amines prepared by reaction of 2-chloroacrylonitrile with monosubstituted hydrazines, it will be appreciated that the reaction may produce 3- or 5- aminopyrazoles. Evidence to date—see *Synthesis* (1976) 52 by G. Ege—indicates that the most likely reaction product is the 3-aminopyrazole and this assumption has therefore been followed in the present specification. However, the evidence for this structure is not unequivocal and, if subsequent research should determine that the 5-aminopyrazole is actually produced, it will be understood that products derived from the foregoing reaction will be similarly 5-substituted.

The intermediates of formula (VI) except when Ar is a pyrazolyl substituted by a pyridyl group, are novel and are provided in a further aspect of the invention.

Compounds of formula (I) have been shown to be useful in the prophylactic and therapeutic treatment of immediate hypersensitivity diseases including asthma and in the alleviation of *status asthmaticus*. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The following Examples will further illustrate the invention.

EXAMPLE 1

(a) 1-Methyl-3-Aminopyrazole

2-Chloroacrylonitrile (175 g, 2 mol) was added slowly to a solution of methyl hydrazine (92 g, 2 mol) and potassium carbonate (280 g, 2 mol) in water (1,000 ml) cooled at 0° C. under nitrogen. The solution was maintained at 0°–5° C. for 1½ hours and then heated at 40°–50° C. for 2 hours. Continuous extraction of the reaction mixture with ethyl acetate, and evaporation of the dried extract, gave 1-methyl-3-aminopyrazole, b.p. 62°–66° C./5 mm, 146 g, as a pale yellow oil.

Analysis: $C_4H_7N_3$ requires: C 49.5; H 7.3; N 43.3%. Found: C 49.3; H 7.5; N 43.5%.

(b) N(1-Methylpyrazol-3-yl)-2-Methylpropanamide isoButyric anhydride (23.8 g, 0.15 mol), and 3-amino-1-methylpyrazole (11.7 g, 0.12 mol) were heated together at 78° C. in benzene for 2 hours. Solvent and excess of reagent were removed in vacuo and the residue distilled at 124°–128° C./0.05 mm. The distillate, 14.4 g, solidified on standing and a sample separated from ether/petrol (40°–60° C.) as needles, m.p. 82°–83° C.

(c) N-Benzyl-N(1-methylpyrazol-3-yl)-2-Methylpropanamide

The pyrazole (3 g, 0.018 mol) in dry DMF (20 ml) was maintained at 0° C. during the addition of 50% sodium hydride (1 g, 0.021 mol). After a further 1 hour at 0° C., benzylbromide (3.5 g, 0.0205 mol) was added and the mixture allowed to cool to room temperature during 2 hours. Water was added and the oil which separated was isolated in ether. Evaporation of the dried extract gave a solid which was recrystallized from ether/petrol (40°–60° C.) as white needles, 2.9 g, m.p. 81°–82° C.

Analysis: $C_{15}H_{19}N_3O$ requires: C 70.1; H 7.45; N 16.35%. Found: C 70.0; H 7.45; N 16.6%.

EXAMPLES 2 to 35

The following pyrazoles were prepared using similar procedures to that described in Example 1. All references to boiling points are to air-bath temperatures.

N-Butyl-N-(1-methylpyrazol-3-yl)acetamide. b.p. 170° C./0.1 mm.
N-Butyl-N-(1-methylpyrazol-3-yl)-2-methylpropanamide. m.p. 43°–47° C.
N-Butyl-N-(1-methylpyrazol-3-yl)cyclohexane carboxamide. m.p. 82°–84° C.
1-Ethoxycarbonyl-N-(1-methylpyrazol-3-yl)heptanamide. m.p. 83°–84° C.
N-Benzyl-N-(1-methylpyrazol-3-yl)benzamide. m.p. 129°–130° C.
N-Decyl-N-(1-methylpyrazol-3-yl)benzamide. m.p. 65°–67° C.
N-Butyl-N-(1-methylpyrazol-3-yl)benzamide. m.p. 63°–65° C.
N-Methyl-N-(1-methylpyrazol-3-yl)-2-methylpropanamide. m.p. 40°–42° C.
N-Butyl-N-(1-methylpyrazol-3-yl)cyclobutyl carboxamide. m.p. 69°–71° C.
N-Hexyl-N-(1-methylpyrazol-3-yl)acetamide. b.p. 165°–170° C./0.1 mm.
N-Methyl-N-(1-methylpyrazol-3-yl)adamantane carboxamide. m.p. 112°–114° C.
N-Butyl-N-(1-methylpyrazol-3-yl)crotonamide. m.p. 35°–38° C.
N-Benzyl-N-(1-methylpyrazol-3-yl)-2-methylpropanamide. m.p. 81°–82° C.
2-Acetoxy-N-(1-methylpyrazol-3-yl)propanamide. b.p. 170° C./0.5 mm.
N-Methyl-N-(1-methylpyrazol-3-yl)cyclohexane carboxamide. m.p. 66°–69° C.
1-Carboxy-N-(1-methylpyrazol-3-yl)heptanamide. m.p. 132°–136° C.
N-(o-Chlorobenzyl)-N-(1-methylpyrazol-3-yl)benzamide. m.p. 148°–149° C.
N-Methyl-N-(1-methylpyrazol-3-yl)heptanamide. m.p. 23°–25° C.
N-Methyl-N-(1-methylpyrazol-3-yl)phenylacetamide. m.p. 49°–51° C.
N-Hexyl-N-(1-methylpyrazol-3-yl)heptanamide. b.p. 160° C./0.2 mm.
N-Hexyl-N-(1-methylpyrazol-3-yl)phenylacetamide. b.p. 190° C./0.5 mm.
2-Acetoxy-N-butyl-N-(1-methylpyrazol-3-yl)propanamide. m.p. 50°–52° C.
1-carboxy-N-(1-methylpyrazol-3-yl)propanamide. m.p. 168°–170° C.
N-(1-Methylpyrazol-3-yl)-N-(2-propenyl)cyclohexane carboxamide. m.p. 82°–83° C.
N-(1-Hexyl)-N-(1-methylpyrazol-3-yl)-2-methylpropanamide. m.p. 34°–35° C.
N-(4-Bromophenyl)methyl-N-(1-methylpyrazol-3-yl)acetamide. m.p. 59°–60° C.
N-Phenylmethyl-N-(1-phenylpyrazol-3-yl)cyclohexane carboxamide. m.p. 109°–110° C.
N-(1-Butylpyrazol-3-yl)-N-(hexyl)cyclopropane carboxamide. b.p. 150° C. @ 0.13 mm Hg.
N-(1-Butyl)-N-(1-methylpyrazol-3-yl)cyclopentane carboxamide. m.p. part 62°–64° C. and part 68°–69° C.
N-(1-Butylpyrazol-3-yl)-N-(methyl)cyclopropane carboxamide. b.p. 130° C. @ 0.15 mm Hg.
N-(1-Methylpyrazol-3-yl)-N-(phenylmethyl)cyclopentane carboxamide. m.p. 88° C.
N-Methyl-N-(1-phenylpyrazol-3-yl)acetamide. m.p. 67°–67.5° C.
N-(1-Hexyl)-N-(1-phenylpyrazol-3-yl)cyclohexane carboxamide. m.p. 57°–58° C.
N-(2-Methylprop-1-yl)-N-(1-methylpyrazol-3-yl)heptanamide. b.p. 123°–126° C.

EXAMPLE 36

N-Phenylmethyl-N-1,3,5-trimethylpyrazol-4-ylheptanamide 1,3,5-Trimethyl-4-pyrazoleamine (4.17 g) in pyridine (40 cc.) was treated with heptanoic anhydride (8.9 g) and stirred at room temperature overnight. Water was then added and the resulting solid was collected, and recrystallised from chloroform/hexane, 6.4 g, m.p. 78°–79° C.

1,3,5-Trimethylpyrazol-4-ylheptanamide (2.37 g) was dissolved in dry DMF (40 ml) at 0° C. and sodium hydride (0.58 g, 50% dispersion) was added slowly. After 1 hour at 0° C., benzyl bromide (11.88 g) was added. After a further hour water was added and the product was isolated in ethyl acetate. Evaporation of the extract gave an oil b.p. 170° C. (air-bath)/0.15 mm.

Analysis: $C_{20}H_{29}N_3O$ requires: C 13.35; H 8.9; N 12.8%. Found: C 13.55; H 9.1; N 12.7%.

EXAMPLE 37

N-(n-Butyl)-N-(1,3,5-trimethylpyrazol-4-yl)cyclohexane carboxamide

4-Amino-1,3,5-trimethylpyrazole (4.17 g) was reacted with cyclohexane carboxylic acid chloride (5.37 g) in dry pyridine (40 ml) for 2½ hours at room temperature. Water was added with resultant precipitation of N-(1,3,5-trimethylpyrazol-4-yl)cyclohexane carboxamide, 4.7 g., m.p. 182° C.

The amide (2.5 g) was suspended in dry DMF (50 cc) and sodium hydride (0.61 g, 50% dispersion) was added slowly. After 1 hour the mixture was cooled in ice and butyliodide (2.13 g) was added. After 3 hours water was added and the product was isolated in ethyl acetate as an oil, b.p. 135° C. (air-bath/)/0.05 mm, 2.7 g.

Analysis: $C_{17}H_{29}N_3O$ requires: C 70.1; H 10.0; N 14.4%. Found: C 70.3; H 9.8; N 14.4%.

EXAMPLE 38

N-(2-Chlorophenyl)methyl-N-(1,3,5-trimethylpyrazol-4-yl)cyclohexane carboxamide. m.p. 121°–122° C. was prepared as in Example 36.

EXAMPLE 39

N-(4-Chlorophenyl)methyl-N-(1,3,5-trimethylpyrazol-4-yl)heptanamide. b.p. 187°–191° C.(air-bath)/0.15 mm was similarly prepared.

EXAMPLE 40

5-Amino-1-methyl-3-phenylpyrazole was prepared according to Gazz. Chim. Ital. 98, 569 (1968) m.p. 128°–129° C.

EXAMPLE 41

N-(1-Hexyl)-N-(1-methyl-3-phenylpyrazol-5-yl)cyclopentane carboxamide

5-Amino-1-methyl-3-phenylpyrazole (3.75 g) in dry pyridine was treated with cyclopentane carboxylic acid chloride (3.14 g) and kept at room temperature for 2 hours. The solvent was then removed in vacuo and the residue dissolved in ethyl acetate. The washed and dried solution was then evaporated to leave a solid 4.8 g, m.p. 160° C.

The amide (2.0 g) was alkylated with hexyliodide as described in previous Example 37. The product was isolated as a solid. m.p. 27°–37° C.

EXAMPLE 42

N-methyl-N-(1-methyl-3-phenylpyrazol-5-yl)cyclopentane carboxamide. m.p. 65°–69° C. was prepared as described in Example 41.

EXAMPLE 43

N-(2-Butyl)-N-(1-methylpyrazol-3-yl)heptanamide

3-Amino-1-methylpyrazole (9.7 g) in DMF (100 cc) and 2-bromobutane (10 cc) was treated with potassium carbonate and heated at 100° C. for 5 hours. Water was then added and the product was isolated in ether, 6.07 g, b.p. 80° C./0.25 mm.

The amine (1.53 g) in dry pyridine (10 cc) was treated with heptanoic anhydride (2.66 g) stirred at room temperature for 15 hours, and then for 4 hours at 50° C. and 3 hours at 120° C. The product was isolated in the normal way as an oil. b.p. 138°–141° C. (air-bath/0.1 mm. 1.5 g.

Analysis: $C_{15}H_{27}N_3O$ requires: C 67.9; H 10.3; N 15.8%. Found: C 67.7; H 10.3; N 15.7%.

EXAMPLE 44

N-Cyclohexyl-N-(1-methylpyrazol-3-yl)pentanamide m.p. 97.5°–98° C. was prepared as described in Example 43.

EXAMPLE 45

N-(2-Butyl)-N-(1-methylpyrazol-3-yl)cyclohexane carboxamide m.p. 98°–99° C. was similarly prepared.

EXAMPLE 46

N-Butyl-N-(1-methyl-4-chloropyrazol-3-yl)cyclohexane carboxamide

N-Butyl-N-(1-methylpyrazol-3-yl) cyclohexane carboxamide (1.3 g, 0.0049 m) in dry benzene (15 cc) was cooled at 0° C. while sulphuryl chloride (0.67 g, 0.0049 m) was added slowly. The cooling bath was then removed and the solution was kept at room temperature for 12 hours. The solvent was then evaporated and the residue crystalled from ether/petrol (40°–60° C.) as white prisms, 1.0 g, m.p. 110°–112° C.

EXAMPLE 47

N-Hexyl-N-(1-methyl-4-chloropyrazol-3-yl)acetamide b.p. 130° C. (air bath)/1 mm; m.p. <room temperature, was similarly prepared.

EXAMPLES 48–53

The amides of Examples 5, 17 and 24 were alkylated with methyl iodide or n-butyl bromide in the presence of sodium hydride using the procedure generally outlined in Example 1 to give the following alkylated products:

1-Ethoxycarbonyl-N-methyl-N-(1-methylpyrazol-3-yl)-heptanamide;
1-Carboxy-N-methyl-N-(1-methylpyrazol-3-yl)-heptanamide;
1-Carboxy-N-methyl-N-(1-methylpyrazol-3-yl)-propanamide;
1-Ethoxycarbonyl-N-n-butyl-N-(1-methylpyrazol-3-yl)-heptanamide;
1-Carboxy-N-n-butyl-N-(1-methylpyrazol-3-yl)-heptanamide;
1-Carboxy-N-n-butyl-N-(1-methylpyrazol-3-yl)-propanamide.

The following Examples 54–60 illustrate pharmaceutical formulations containing the active compound N-(n-butyl)-N-(1,3,5-trimethylpyrazol-4-yl)-cyclohexane carboxamide.

EXAMPLE 54

Soft gelatin capsules were prepared using the following ingredients:

|  | Quantity (mg/capsule) |
| --- | --- |
| Active compound | 20 |
| Propyl gallate | 0.03 |
| Fractionated Coconut Oil B.P.C. | 70 |

The above ingredients were mixed and filled into soft gelatin capsules, the main shell components of which were gelatin and glycerine.

EXAMPLE 55

Hard gelatin capsules were prepared using the following ingredients:

|  | Quantity (mg/capsule) |
|---|---|
| Active compound | 25 |
| Silicon dioxide (fumed) | 25 |
| Lactose | 50 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 56

An ointment was made up from the following ingredients:
Active compound: 2% by weight
Butylated hydroxyanisole B.P.: 0.04% by weight
White soft paraffin: q.s. 100%
The hydroxyanisole was dissolved in the melted paraffin and the active compound then added in, and the mixture allowed to cool.

EXAMPLE 57

A topical cream containing 1% of the compound was prepared as follows:

|  | grams: |
|---|---|
| Active compound | 1 |
| Cetomacrogol 1000 | 3 |
| Cetostearyl alcohol | 10 |
| Liquid Paraffin | 7 |
| Butylated hydroxyanisole B.P. | 0.04 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 58

Suppositories containing 30 and 60 mg. of the compound were prepared as follows:
Active compound: 3 g
Henkel base: 97 g
The active compound was mixed with the Henkel base which had been previously melted using the minimum amount of heat possible. The mixture was then poured into suppository moulds of a nominal capacity of 1 g. or 2 g. as desired, to produce suppositories each containing 30 mg. or 60 mg. of the active compound.

EXAMPLE 59

An aerosol was prepared containing the following ingredients:

|  | Quantity per ml. | |
|---|---|---|
| Active compound | 10.00 | mg. |
| Propylene glycol | 10.00 | mg. |
| Dichlorotetrafluoroethane (Propellant 114) | 500 | mg. |
| Dichlorodifluoromethane (Propellant 12) | 900 | mg. |

The active compound was mixed with the propylene glycol and the mix added to the propellant 114, the mixture cooled to $-15°$ to $-20°$ C. and transferred to a filling device. At the same time a mixture of propellants 114 and 12, previously cooled to $-15°$ to $-20°$ C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 60

Tablets were prepared using the following components:
Active compound: 15.00 mg.
Microcrystalline Cellulose: 240.00 mg.
Sodium Carboxymethyl Starch: 20.00 mg.
Magnesium Stearate: 2.5 mg.
Butylated Hydroxyanisole B.P.: 0.002 mg.
The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:
1. A heteroaryl compound of the formula

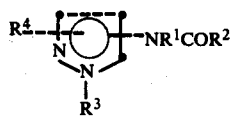

wherein $R^1$ is selected from a group consisting of $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, $R^5$-substituted phenyl-$C_{1-6}$ alkyl and phenyl-$C_{2-6}$-alkenyl, $R^5$-substituted phenyl-$C_{2-6}$ alkenyl; $R^2$ is selected from the group consisting of $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, $R^5$-substituted phenyl, phenyl-$C_{1-6}$ alkyl, $R^5$-substituted phenyl-$C_{1-6}$ alkyl, phenyl-$C_{2-6}$ alkenyl, $R^5$-substituted phenyl-$C_{2-6}$ alkenyl, $C_{1-4}$ alkoxycarbonyl-$C_{1-8}$ alkyl, $C_{2-8}$ carboxyalkyl and acetoxy-$C_{1-4}$ alkyl; $R^3$ is selected from $C_{1-4}$ alkyl and phenyl; and $R^4$ is selected from hydrogen, $C_{1-4}$ alkyl, phenyl and halogen; and $R^5$ is selected from a group consisting of halogen, trifluoromethyl, methyl, methoxy, and nitro; provided that, when the -$NR^1COR^2$ group is in the 5 position, and $R^1$ and $R^2$ are both methyl, $R^3$ cannot be phenyl.

2. A heteroaryl compound of claim 1 having the formula:

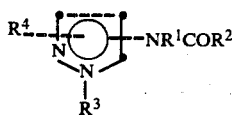

wherein $R^1$ is selected from the group consisting of $C_{1-10}$ alkyl, $C_{3-6}$ alkenyl, $C_{3-8}$ cycloalkyl, benzyl, and benzyl substituted by halogen; $R^2$ is selected from the group consisting of $C_{1-8}$ alkyl, $C_{2-6}$ alkenyl, $C_{3-10}$ cycloalkyl, phenyl, benzyl, $C_{1-4}$ alkoxycarbonyl-$C_{4-8}$ alkyl, $C_{2-8}$ carboxyalkyl and acetoxy-$C_{1-4}$ alkyl; $R^3$ is selected from $C_{1-4}$ alkyl and phenyl; and $R^4$ is selected from hydrogen, $C_{1-4}$ alkyl, phenyl and halogen; provided that, when the -$NR^1COR^2$ group is in the 5 position, and $R^1$ and $R^2$ are both methyl, $R^3$ cannot be phenyl.

3. A heteroaryl compound of the formula:

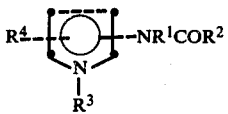

wherein $R^1$ is selected from the group consisting of $C_{1-10}$ alkyl, $C_{3-6}$ alkenyl, $C_{3-8}$ cycloalkyl, benzyl, and benzyl substituted by halogen; $R^2$ is selected from the group consisting of $C_{1-8}$ alkyl, $C_{2-6}$ alkenyl, $C_{3-10}$ cycloalkyl, phenyl, benzyl, $C_{1-4}$ alkoxycarbonyl-$C_{4-8}$ -alkyl, $C_{2-8}$ carboxyalkyl and acetoxy-$C_{1-4}$ alkyl; $R^3$ is selected from $C_{1-4}$ alkyl and phenyl; and $R^4$ is selected from hydrogen, $C_{1-4}$ alkyl, phenyl and halogen; and the acylamino group —$NR^1COR^2$ is attached at the 3- or 5-position of the pyrazole nucleus.

4. A heteroaryl compound of claim 3 wherein $R^3$ is $C_{1-4}$ alkyl; $R^4$ is hydrogen, $C_{1-4}$ alkyl or phenyl; and —$NR^1COR^2$ is a 3-substituent in which $R^1$ is $C_{3-6}$ alkyl, allyl or benzyl and $R^2$ is $C_{3-6}$ alkyl, allyl, benzyl or $C_{3-5}$ cycloalkyl.

5. A heteroaryl compound according to claim 1 being N-butyl-N-(1-methylpyrazol-3-yl)-2-methylpropanamide.

6. A heteroaryl compound according to claim 1 being N-butyl-N-(1-methylpyrazol-3-yl)-cyclohexane carboxamide.

7. A heteroaryl compound according to claim 1 being N-benzyl-N-(1-methylpyrazol-3-yl)benzamide.

8. A heteroaryl compound according to claim 1 being N-butyl-N-(1-methylpyrazol-3-yl)-benzamide.

9. A heteroaryl compound according to claim 1 being N-methyl-N-(1-methylpyrazol-3-yl)adamantane carboxamide.

10. A heteroaryl compound according to claim 1 being N-butyl-N-(1-methylpyrazol-3-yl)-crotonamide.

11. A heteroaryl compound according to claim 1 being N-(o-chlorobenzyl)-N-(1-methylpyrazol-3-yl)-benzamide.

12. A heteroaryl compound according to claim 1 being N-methyl-N-(1-methylpyrazol-3-yl)-heptanamide.

13. A heteroaryl compound according to claim 1 being N-methyl-N-(1-methylpyrazol-3-yl)-phenylacetamide.

14. A heteroaryl compound according to claim 1 being N-hexyl-N-(1-methylpyrazol-3-yl)-heptanamide.

15. A heteroaryl compound according to claim 1 being N-(1-methylpyrazol-3-yl)-N-(2propenyl)-cyclohexane carboxamide.

16. A heteroaryl compound according to claim 1 being N-(1-butylpyrazol-3-yl)-N-(hexyl)cyclopropane carboxamide.

17. A heteroaryl compound according to claim 1 being N-(1-methylpyrazol-3-yl)-N-(phenylmethyl)-cyclopentane carboxamide.

18. A heteroaryl compound according to claim 1 being N-(n-butyl)-N-(1,3,5-trimethylpyrazol-4-yl)-cyclohexane carboxamide.

19. A heteroaryl compound according to claim 1 being N-cyclohexyl-N-(1-methylpyrazol-3-yl)-pentanamide.

20. A compound of the formula:

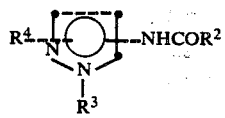

wherein $R^2$ is selected from the group consisting of $C_{1-8}$ alkyl, $C_{2-6}$ alkenyl, $C_{3-10}$ cycloalkyl, phenyl, benzyl, $C_{1-4}$ alkoxycarbonyl -$C_{4-8}$ alkyl, $C_{2-8}$ carboxyalkyl and acetoxy-$C_{1-4}$ alkyl; $R^3$ is selected from $C_{1-4}$ alkyl and phenyl; and $R^4$ is is selected from hydrogen, $C_{1-4}$ alkyl, phenyl and halogen; provided that when the —$NHCOR^2$ group is in the 5 position and $R^2$ is methyl, $R^3$ cannot be phenyl.

21. A compound of claim 3 wherein $R^3$ is $C_{1-4}$ alkyl; $R^4$ is hydrogen, $C_{1-4}$ alkyl or phenyl; and —$NR^1COR^2$ is a 5-substituent in which $R^1$ is $C_{3-6}$ alkyl, allyl or benzyl and $R^2$ is $C_{3-6}$ alkyl, allyl, benzyl or $C_{3-5}$ cycloalkyl.

22. A compound of the formula

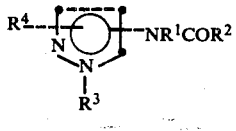

wherein:
$R^1$ is selected from a group consisting of $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, $R^5$-substituted phenyl-$C_{1-6}$ alkyl, phenyl-$C_{2-6}$ alkenyl, $R^5$-substituted phenyl-$C_{2-6}$ alkenyl;
$R^2$ is selected from the group consisting of $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, $R^5$-substituted phenyl, phenyl-$C_{1-6}$ alkyl, $R^5$-substituted phenyl-$C_{1-6}$ alkyl, phenyl-$C_{2-6}$ alkenyl, $R^5$-substituted phenyl-$C_{2-6}$ alkenyl, $C_{1-4}$ alkoxycarbonyl-$C_{1-8}$ alkyl, $C_{2-8}$ carboxyalkyl and acetoxy-$C_{1-4}$ alkyl;
$R^3$ is selected from hydrogen, $C_{1-4}$alkyl, benzyl and phenyl; $R^4$ is selected from hydrogen, $C_{1-4}$ alkyl, benzyl, phenyl and halogen; and $R^5$ is selected from a group consisting of halogen, trifluoromethyl, ethyl, methoxy, and nitro; provided that, when $R^1$ and $R^2$ are both methyl and the —$NR^1COR^2$ group is at the 5-position, $R^3$ cannot be phenyl.

23. A pharmaceutical formulation useful for the treatment of asthma comprising a therapeutically-effective amount of a compound of the formula

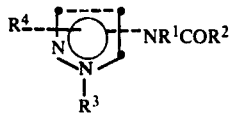

wherein $R^1$ is selected from a group consisting of $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, $R^5$-substituted phenyl-$C_{1-6}$ alkyl, phenyl-$C_{2-6}$ alkenyl, and $R^5$-substituted phenyl-$C_{2-6}$ alkenyl; $R^2$ is selected from the group consisting of $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, $R^5$-substituted phenyl, phenyl-$C_{1-6}$ alkyl, $R^5$-substituted phenyl-$C_{1-6}$ alkyl, phenyl-$C_{2-6}$ alkenyl, $R^5$-substituted phenyl-$C_{2-6}$ alkenyl, $C_{1-4}$ alkoxycarbonyl-$C_{1-8}$ alkyl, $C_{2-8}$ carboxyalkyl and acetoxy-$C_{1-4}$ alkyl; $R^3$ is selected from $C_{1-4}$ alkyl and phenyl; $R^4$ is selected from hydrogen, $C_{1-4}$ alkyl, phenyl and halogen; and $R^5$ is selected from a group consisting of halogen, trifluoromethyl, methyl, methoxy, and nitro; provided that, when the -$NR^1COR^2$ group is in the 5 position, and $R^1$ and $R^2$ are both methyl, $R^3$ cannot be phenyl.

24. A pharmaceutical formulation of claim 23 comprising as an active ingredient a therapeutically effective amount of a compound of formula:

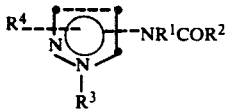

wherein $R^1$ is selected from the group consisting of $C_{1-10}$ alkyl, $C_{3-6}$ alkenyl, $C_{3-8}$ cycloalkyl, benzyl, and benzyl substituted by halogen; $R^2$ is selected from the group consisting of $C_{1-8}$ alkyl, $C_{2-6}$ alkenyl, $C_{3-10}$ cycloalkyl, phenyl, benzyl, $C_{1-4}$ alkoxycarbonyl-$C_{4-8}$ alkyl, $C_{2-8}$ carboxyalkyl and acetoxy-$C_{1-4}$ alkyl; $R^3$ is selected from $C_{1-4}$ alkyl and phenyl; and $R^4$ is selected from hydrogen, $C_{1-4}$ alkyl, phenyl and halogen; provided that, when the -$NR^1COR^2$ group is in the 5 position, and $R^1$ and $R^2$ are both methyl, $R^3$ cannot be phenyl.

25. A method of treating a mammal suffering from, or susceptible to, asthma which comprises administering to the mammal a therapeutically-effective amount of a compound of the formula

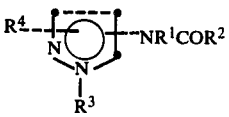

wherein $R^1$ is selected from a group consisting of $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, $R^5$-substituted phenyl-$C_{1-6}$ alkyl and phenyl-$C_{2-6}$ alkenyl, $R^5$-substituted phenyl-$C_{2-6}$ alkenyl; $R^2$ is selected from the group consisting of $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, $R^5$-substituted phenyl, phenyl-$C_{1-6}$ alkyl, $R^5$-substituted phenyl-$C_{1-6}$ alkyl, phenyl-$C_{2-6}$ alkenyl, $R^5$-substituted phenyl-$C_{2-6}$ alkenyl, $C_{1-6}$ alkoxycarbonyl-$C_{1-4}$ alkyl, $C_{2-8}$ carboxyalkyl and acetoxy-$C_{1-4}$ alkyl; $R^3$ is selected from $C_{1-4}$ alkyl and phenyl; $R^4$ is selected from hydrogen, $C_{1-4}$ alkyl, phenyl and halogen; and $R^5$ is selected from a group consisting of halogen, trifluoromethyl, methyl, methoxy, and nitro; provided that, when the -$NR^1COR^2$ group is in the 5 position, and $R^1$ and $R^2$ are both methyl, $R^3$ cannot be phenyl.

26. A method of claim 25 which comprises administering to the mammal a therapeutically effective amount of a compound of the formula:

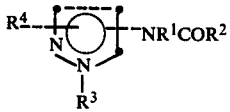

wherein $R^1$ is selected from the group consisting of $C_{1-10}$ alkyl, $C_{3-6}$ alkenyl, $C_{3-8}$ cycloalkyl, benzyl and benzyl substituted by halogen; $R^2$ is selected from the group consisting of $C_{1-8}$ alkyl, $C_{2-6}$ alkenyl, $C_{3-10}$ cycloalkyl, phenyl, $C_{1-4}$ alkoxycarbonyl-$C_{4-8}$ alkyl, $C_{2-8}$ carboxyalkyl and acetoxy-$C_{1-4}$ alkyl; $R^3$ is selected from $C_{1-4}$ alkyl and phenyl; and $R^4$ is selected from hydrogen, $C_{1-4}$ alkyl, phenyl and halogen.

* * * * *

UNITED STATES PATENT AND TRADEMARK OFFICE
CERTIFICATE OF CORRECTION

PATENT NO. : 4,166,123

DATED : August 28, 1979

INVENTOR(S) : Roger G. Harrison, William B. Jamieson, John C. Saunders, and William J. Ross It is certified that error appears in the above-identified patent and that said Letters Patent are hereby corrected as shown below:

Column 1, line 50, "prazolyl" should read -- pyrazolyl --.

Column 3, line 19, "atoms" should read -- atom --.

Columns 10-14, claims 1-3, 20, and 22-26, that part of the structural formula reading " 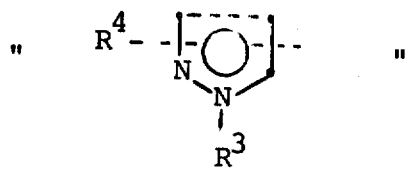 "

should read

-- 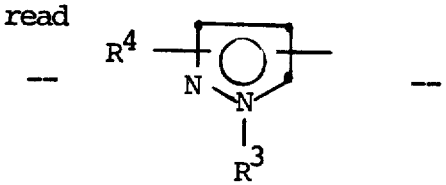 --

UNITED STATES PATENT AND TRADEMARK OFFICE
CERTIFICATE OF CORRECTION

PATENT NO. : 4,166,123
DATED : August 28, 1979
INVENTOR(S) : Roger G. Harrison, William B. Jamieson, John C. Saunders, and William J. Ross It is certified that error appears in the above-identified patent and that said Letters Patent are hereby corrected as shown below:

Column 12, line 2, "-(2propenyl)-" should read -- -(2-propenyl)- --; line 29, "$R^4$ is is" should read -- $R^4$ is --; line 59, "$C_{1-4}$alkyl" should read -- $C_{1-4}$ alkyl --.

Column 13, lines 43-45, "provided that, when the $-NR^1COR^2$ group is in the 5 position, and $R^1$ and $R^2$ are both methyl, $R^3$ cannot be phenyl." should read -- admixed with a pharmaceutically acceptable carrier therefor. --.

Column 11, lines 22-27, in claim 3, should read

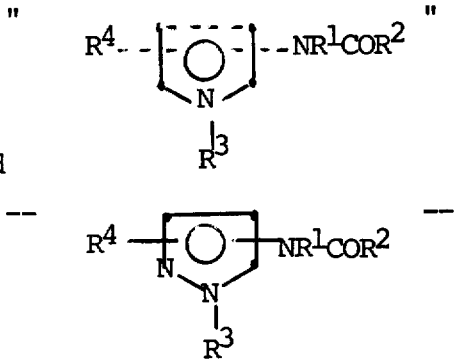

Signed and Sealed this

Nineteenth Day of February 1980

[SEAL]

Attest:

SIDNEY A. DIAMOND

Attesting Officer

Commissioner of Patents and Trademarks